United States Patent [19]

Colle et al.

[11] 4,224,050
[45] Sep. 23, 1980

[54] CHLOROACETANILIDES HAVING A SELECTIVE HERBICIDAL ACTIVITY, ORTHO-ALKENYL-SUBSTITUTED ANILINES, INTERMEDIATES IN THE SYNTHESIS OF SAID HERBICIDAL CHLOROACETANILIDES, AND METHODS FOR THEIR PREPARATION

[75] Inventors: Roberto Colle, Milan; Franco Gozzo, Saronno; Giovanni Camaggi, Lodi; Giorgio Siddi, S. Donato Milanese, all of Italy

[73] Assignee: Montedison S.p.A., Milan, Italy

[21] Appl. No.: 875,893

[22] Filed: Feb. 7, 1978

[30] Foreign Application Priority Data

Feb. 10, 1977 [IT] Italy ............................... 20153 A/77
May 20, 1977 [IT] Italy ............................... 23809 A/77
Oct. 20, 1977 [IT] Italy ............................... 28817 A/77

[51] Int. Cl.² ..................... A01N 9/12; A01N 9/20; C07C 103/22
[52] U.S. Cl. ............................. 71/98; 71/105; 71/106; 71/107; 71/111; 71/115; 71/118; 260/558 A; 260/558 P; 260/561 HL; 260/562 B; 260/562 P; 260/562 R; 260/576; 260/573; 260/577; 560/1; 560/43; 560/106; 560/121; 560/123; 560/221; 560/250; 562/433; 562/456
[58] Field of Search ............... 71/118, 105, 115, 98, 71/111, 106, 107; 260/562 B, 576, 577, 573, 562 R, 562 E, 558 A, 558 P, 568 E, 561 HL; 560/1, 121, 123, 106, 250, 221, 43; 562/433, 456

[56] References Cited

U.S. PATENT DOCUMENTS

| | | | |
|---|---|---|---|
| 3,547,620 | 12/1970 | Olin | 71/118 |
| 3,557,210 | 1/1971 | Hamm | 71/118 X |
| 3,769,301 | 10/1973 | Olin | 71/118 X |
| 3,829,306 | 8/1974 | Ratts | 71/118 X |
| 3,901,685 | 8/1975 | Ratts | 71/118 |
| 3,952,056 | 4/1976 | Vogel et al. | 71/118 |
| 4,001,325 | 1/1977 | Bluestone et al. | 71/118 X |
| 4,008,066 | 2/1977 | Moser | 71/118 X |

FOREIGN PATENT DOCUMENTS

| | | | |
|---|---|---|---|
| 733524 | 5/1966 | Canada | 71/118 |
| 2242420 | 3/1973 | Fed. Rep. of Germany | 260/562 B |
| 7301481 | 8/1973 | Netherlands | 71/118 |

OTHER PUBLICATIONS

Jolidon et al.; Chimia 30(1976), pp. 23–25.
Takamatsu et al.; Tet. Letters 48(1971), pp. 4661–4664.
Schmid et al.; Helv. Chim. Acta 56(1973), pp. 105–124.

*Primary Examiner*—Arthur P. Demers
*Attorney, Agent, or Firm*—Stevens, Davis, Miller & Mosher

[57] ABSTRACT

Chloroacetanilides are disclosed having the general formula:

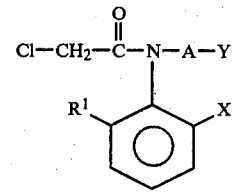

wherein
$R^1$ = H, or alkyl with 1–5 carbon atoms, or X;
X = alkenyl, and preferably

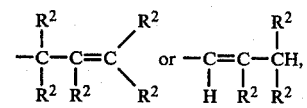

in which the various $R^2$, which may be equal to or different from each other, are H or an alkyl with 1–3 carbon atoms;
A = alkylene, optionally substituted, of the formula:

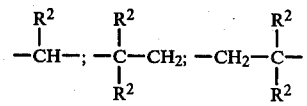

in which the various $R^2$, which may be equal to or different from each other, have the meanings specified above; and
Y = H; alkyl with 1–5 carbon atoms; alkenyl with 2–5 carbon atoms; alkinyl with 2–5 carbon atoms; phenyl; cycloalkyl with 3–8 carbon atoms; halogen;

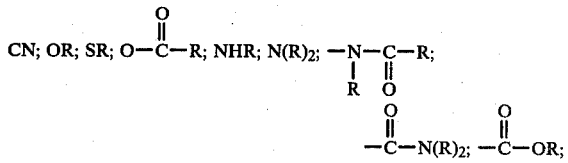

wherein R = H; alkyl with 1–5 carbon atoms; alkenyl or alkinyl with 2–5 carbon atoms; cycloalkyl with 3–8 carbon atoms; phenyl;

The chloroacetanilide derivatives are useful in combatting infestations of infesting monocotyledons and dicotyledons during pre-emergence, by spreading the chloroacetanilide derivative on the soil adjacent thereto in quantities ranging from 0.25 kg/ha upwards.

20 Claims, No Drawings

CHLOROACETANILIDES HAVING A SELECTIVE HERBICIDAL ACTIVITY, ORTHO-ALKENYL-SUBSTITUTED ANILINES, INTERMEDIATES IN THE SYNTHESIS OF SAID HERBICIDAL CHLOROACETANILIDES, AND METHODS FOR THEIR PREPARATION

The present invention relates to new chloroacetanilides. More particularly, it relates to a new class of herbicidal chloroacetanilides that are only slightly toxic for maize (corn), and it also relates to preparatory methods for obtaining said herbicides.

This invention also relates to the ortho-alkenyl-substituted anilines which are intermediates in the synthesis of the above said herbicidal chloroacetanilides, and also to the methods of preparation for obtaining them.

The herbicidal chloroacetanilides of the general formula:

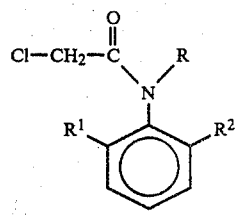
(I)

wherein $R^1$ and $R^2$ are alkyl groups, while R has different meanings to differentiate the various classes from each other, are known, for instance, from Italian Pat. No. 762,131 and from U.S. Pat. No. 3,403,994 in the name of Monsanto Company, or from German Pat. No. 2,328,340 in the name of CIBA Co., or from U.S. Pat. No. 3,780,090 in the name of Sumitomo Company. Some of the products according to the general formula (I) are available on the market, such as for instance ALACHLOR (or Lasso) and BUTACHLOR (or Machete) produced by Monsanto. All of these compounds, although displaying a considerable herbicidal activity, have proved to be toxic for maize.

We have now found, and this forms a principal object of this invention, chloroacetanilides of the general formula (II):

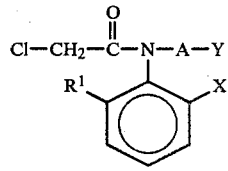
(II)

wherein
$R^1$ = H; alkyl with 1-5 carbon atoms; X;
X = alkenyl, preferably

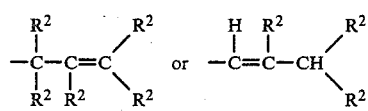

wherein the various $R^2$, equal to or different from each other, are H or alkyl with 1-3 carbon atoms;
A = alkylene

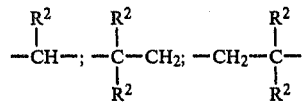

wherein the various $R^2$, equal to or different from each other, have the meanings indicated above; and
Y = H; alkyl with 1-5 carbon atoms; alkenyl or alkinyl with 2-5 carbon atoms; phenyl; cycloalkyl; halogen; or saturated or unsaturated heterocyclic group containing from 1 to 3 hetero-atoms;

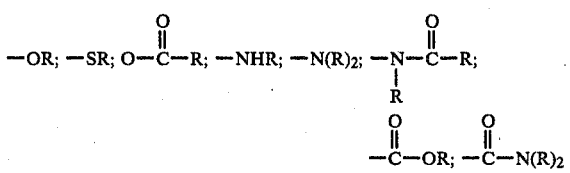

wherein R = H; alkyl; alkenyl; alkinyl; cycloalkyl; phenyl; a saturated or unsaturated heterocyclic group containing from 1 to 3 hetero-atoms; CN, which are endowed with herbicidal activity, and at the same time develop little toxicity toward maize.

Intermediates for the synthesis of the chloroacetanilides of the general formula (II) are the ortho-substituted anilines of general formulae (III) and (IV):

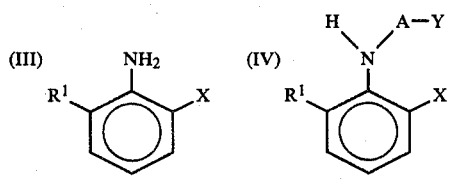

wherein $R^1$, X, A and Y have the same meanings as those indicated above in the general formula (II).

Some of the anilines of the general formulae (III) and (IV) may be prepared according to known methods (see for instance Helvetica Chimica Acta, 56, 1973, page 105; Journal of Organic Chemistry 22, 1957, page 1418; Journal of the American Chemical Society 83, 1961, page 3319; and Chimia 30 (1), 1976, pages 21-25), one common step consisting of an allylic transposition achieved by the action of zinc chloride on N(alkenyl)-aniline.

During our study of the herbicidal chloroacetanilides, we observed that many of the anilines, ortho-substituted in positions 2 and 6 and in which at least one substituent is an alkenyl group, and which serve as the starting material in the synthesis, are not known; and moreover, that there is not known a general and at the same time economic process for their preparation.

For example, 2-ethyl-6-(2'-propenyl)-aniline and 2-ethyl-6-(1'-methyl-2'-propenyl)-aniline were not previously known.

Thus, another principal object of this invention are ortho-substituted anilines of the general formula (IVa):

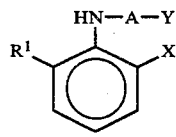 (IVa)

wherein:
$R^1$ = alkyl with 1–5 carbon atoms or X;
X = alkenyl of the formula:

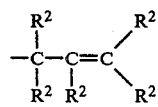

with $R^2$ equal to or different from each other, and representing H or alkyl with 1–3 carbon atoms;
A = alkylene, optionally substituted, of the formula:

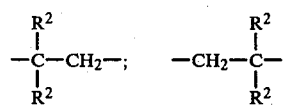

wherein $R^2$ has the meaning indicated hereinabove;
Y = H; alkyl with 1–5 carbon atoms; alkenyl; alkinyl; phenyl; cycloalkyl; halogen; a saturated or unsaturated heterocyclic group; —OR; —SR;

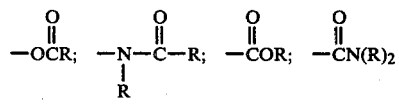

wherein R = H; alkyl with 1–5 carbon atoms; alkenyl or alkinyl with 2–5 carbon atoms; cycloalkyl; phenyl; a saturated or unsaturated heterocyclic group containing from 1 to 3 hetero-atoms; CN; and
A–Y together may be = H in which case $R^1$ is different from methyl.

Another object of this invention is a general and economically convenient (i.e., cheap) process for obtaining the anilines of the general formula (IVa), which process consists in treating N-substituted anilines of the general formula:

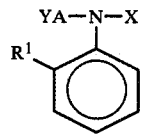

wherein X, A, and Y have the same meanings as those specified above in the general formula (IVa); $R^1$, besides the meanings of the general formula above, may be H and moreover A and Y together may be H or may have the same meaning as X, in an aqueous solution with a strong acid, such as sulphuric acid, phosphoric acid, a hydro-halogen acid, in equimolecular quantities with the N-substituted aniline in order to form its salt, and in then heating the salt thus obtained in an aqueous solution at 100°–160° C. for a time between 1 and 10 hours.

In the case in which $R^1$ is H and AY is equal to X, 2,6-di-(2-alkenyl) substituted anilines will be obtained, while in the case in which AY is different from H and from X, ortho-di-substituted anilines having the AY group bound to nitrogen will be obtained:

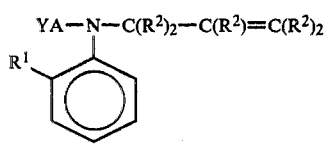

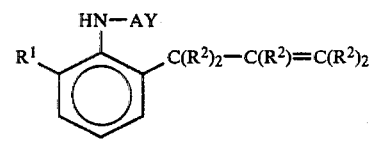

The anilines of general formula (IVa) may also be obtained by reacting ortho-alkenyl-substituted anilines of general formula (III) with a Z-A-Y-haloderivative (Z = halogen) in the presence of a hydrohalogen acid (HZ)-accepting base. (Scheme 1 below, reaction a).

The reaction mixture is washed with water and is then extracted with a low-boiling solvent. After dehydration, the extract is subjected to distillation in order to obtain the intermediate (IVa).

As a haloderivative, Z-A-Y may represent an alkyl-, alkenyl-, alkinyl, a cycloalkyl-, a heterocycloalkyl-, alkyl- aminoalkyl-, a cyanoalkyl-halide or an alkoxyalkyl, alkylthio- alkyl-halide, or a haloacetate or a haloacetamide.

Another object of this invention is that of providing ortho-1-alkenyl substituted anilines of the general formula (IVb):

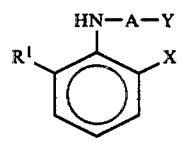 (IVb)

wherein:
A—Y = H; or
A = alkylene, optionally substituted, of the type

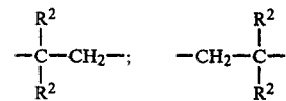

where $R^2$ = H or $CH_3$;
Y = $OR^3$ wherein $R^3$ = alkyl with 1–5 carbon atoms;
$R^1$ = H; alkyl with 1–5 carbon atoms; X; and
X = 1-alkenyl of formula:

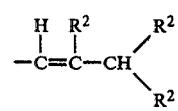

Ortho-1-alkenyl substituted anilines are useful intermediates for the preparation of herbicidal chloroacetanilides of the general formula (II) wherein X =

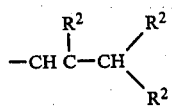

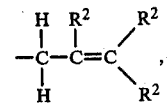

wherein $R^2$=H or $CH_3$.

The preparation process for these anilines (which too forms an object of this invention) consists or consists essentially in treating anilines of general formula (IVa) where X is a 2-alkenyl of the formula:

in an alcoholic medium with an excess of alkali, at a temperature between 100° and 160° C. and for a time of from 1 to 5 hours, ortho-1-alkenyl-substituted anilines of general formula (IVa) being the products of this reaction (Scheme 1 below, reaction b).

The ortho-alkenyl substituted anilines of general formula (IVa) and (IVb) as reported below in Table 1 were prepared according to one of the methods hereinabove described.

TABLE 1

| Compound | $R^1$ | X | A—Y | B.p. °C.(mmHg) | IR-$(dm^{-1})$* | NMR*($\delta$,ppm)** |
|---|---|---|---|---|---|---|
| A | $C_2H_5$ | $CH_2$—CH=$CH_2$ | H | 128–(15) | 3470,3390 ($\nu NH_2$) | 3.6 ($NH_2$) 1.25 (t), |
|  |  |  |  |  | 1630 ($\rangle C=C\langle$) | 2.5(q) ($C_2H_5$); |
|  |  |  |  |  | 998,915 ($\nu$-CH=$CH_2$) | 3.3(m), 4.85–6.3(m) ($CH_2$—CH=$CH_2$); 6.5–7.1 (H aromatics) |
| B | $CH_3$ | $CH_2$—CH=$CH_2$ | H |  |  | 3.45 ($NH_2$); 2.05(s) ($CH_3$) |
| C | $C_2H_5$ | $CH_3$<br>\|<br>CH—CH=$CH_2$ | H |  |  | 3.45 ($NH_2$); 1.3(d), 3.35(q), 4.7–6.1(m) (CH—CH=$CH_2$)<br>\|<br>$CH_3$ |
| D | $CH_3$ | $CH_3$<br>\|<br>CH—CH=$CH_2$ | H |  |  | 3.45 ($NH_2$); 2.05(s) ($CH_3$) |
| E | $CH_2$—CH—$CH_2$ | $CH_2$—CH=$CH_2$ | H | 90 (05) | 3450,3380 ($\nu NH_2$) 1630,1615 ($\rangle C=C\langle$) 992–910 ($\nu CH=CH_2$) |  |
| F | $CH_3$ | $CH_2$—CH=$CH_2$ | $CH_2$—$CH_2OCH_3$ | 95–97 (0.1) | 3400 ($\nu NH$) 1635,1615 ($\rangle C=C\langle$) 992,910 ($\nu$-CH=$CH_2$) |  |
| G | $C_2H_5$ | $CH_2$—CH=$CH_2$ | $CH_2$—$CH_2OCH_3$ | 88 (0.05) | 3410 ($\nu NH_2$) 1682,1632,1610,1000 ($\rangle C=C\langle$) 900,908 (—CH—$CH_2$) |  |
| H | $CH_3$ | $CH_2$—CH=$CH_2$ | CH—$CH_2$—$OCH_3$<br>\|<br>$CH_3$ | 90 (0.1) |  | 1.2(d) 2.8–3.8(a), 2.3(s) (NH—CH—$CH_2$—$OCH_3$)<br>\|<br>$CH_3$<br>4.2–6.4(m) (CH=$CH_2$) |
| I | $C_2H_5$ | $CH_2$—CH=$CH_2$ | CH—$CH_2OCH_3$<br>\|<br>$CH_3$ | 105–107 (0.1) |  | 1.2(d), 2.8–3.8(m), 2.3(s) (NH—CH—$CH_2$—$OCH_3$);<br>\|<br>$CH_3$<br>4.2–6.4(m) (CH=$CH_2$); 2.7(q), 1.3(t) ($C_2H_5$) |
| J | $CH_3$ | CH=CH—$CH_3$ | H | 126–130(20) | 3470,3380 ($\nu NH_2$) | 1.8(d,J=6Hz) ($CH_3$ vinylic), |

TABLE 1-continued

| Compound | $R^1$ | X | A—Y | B.p. °C.(mmHg) | IR-(dm$^{-1}$)* | NMR*(δ,ppm)** |
|---|---|---|---|---|---|---|
| K | $C_2H_5$ | CH=CH—$CH_3$ | H | 132–136 (20) | 1615,965 (CH=CH—$CH_3$) 3470,3380 ($\nu NH_2$) 1615,965 ($\nu$CH=CH—$CH_3$) | 3.4 ($NH_2$) 2.0(s) ($CH_3$-φ) 1.8(d,J-6Hz) ($CH_3$ vinylic), 3.4 ($NH_2$); 2.7(q), 1.3(t) ($C_2H_5$-φ) |
| L | CH=CH—$CH_3$ | CH=CH—$CH_3$ | H | m.p. = 62–64° C. | 3430,3340,3230 ($\nu NH_2$) 1635,960 ($\nu$CH=CH—$CH_3$) | 1.9(d) ($CH_3$ vinylic); 3.76 ($NH_2$) |
| M | $CH_3$ | CH=CH—$CH_3$ | $CH_2$—$CH_2OCH_3$ | 98–102 (0.1) | 3380 ($\nu$NH) 1590,980 (CH=CH—$CH_3$) 1120 ($\nu$C—O—C) | 1.9(d) ($CH_3$ vinylic) 2.36(s) ($CH_3$-φ) |

*Only the more representative spectroscopic data are reported
**(s) singlet, (d) = doublet, (t) = triplet, (q) = quartet, (m) = multiplet.

Chloroacetanilides of general formula (II) are prepared by reacting anilines of general formula (IVa) and (IVb) with chloroacetyl-chloride in the presence of a hydrohalogen acid-accepting base (Scheme below, reaction c).

Chloroacetanilides of general formula (II) may also be prepared starting from ortho-alkenyl-substituted anilines, by following one of the processes schematically summarized below in Scheme 2.

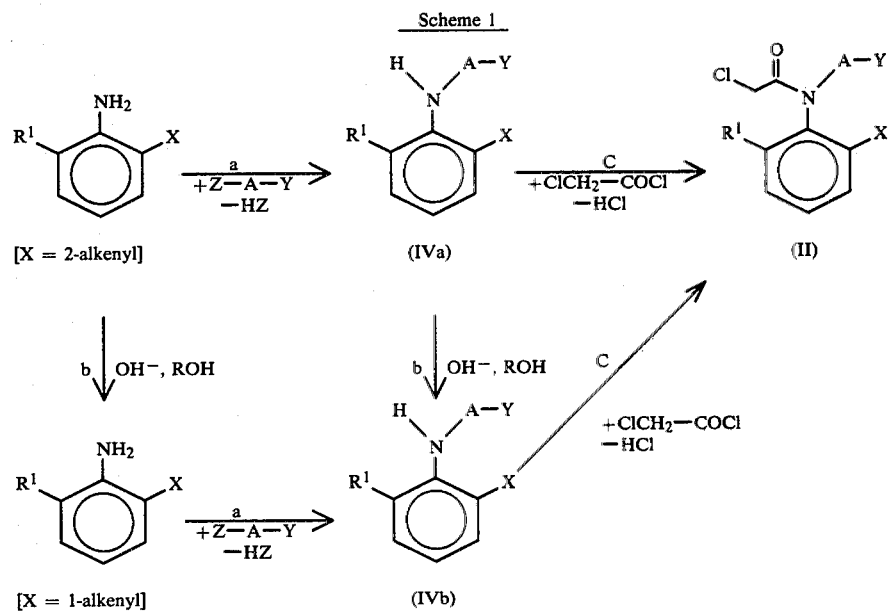

Scheme 1

Scheme 2

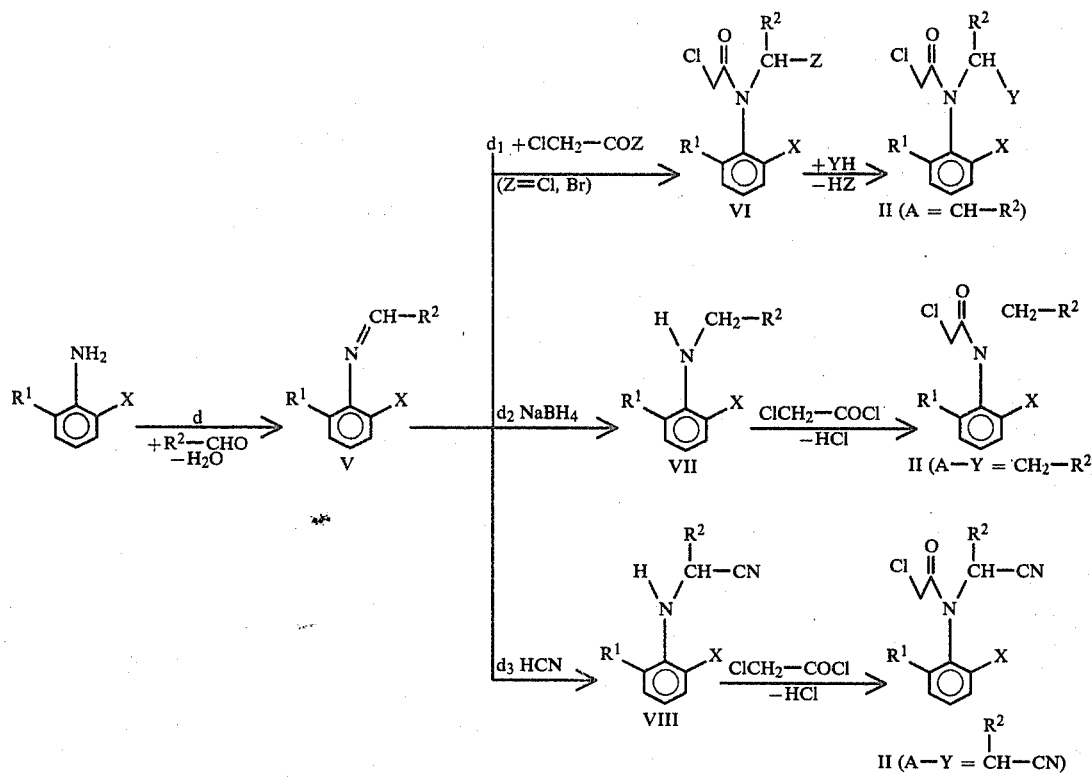

The first reaction of the sequence reported above in Scheme 2 (reaction d) is attained by reacting an ortho-alkenyl aniline with an aldehyde in an inert solvent, preferably in the presence of small quantities of a methanolic solution of triethylamine, the azaalkene (V) being the product of the reaction.

The compounds of this invention are obtained from azaalkene (V) passing through one of the following steps:

$d_1$—Addition of a halide of chloroacetic acid, in order to obtain type (VI) intermediates which may be condensed with alcohols, thiols, amines, carboxylic acids (YH) to yield compounds of the general formula (II) wherein $A = -CHR^2$.

$d_2$—Hydrogenation of the $C = N$ double bond, with a selective reducer, such as for instance sodium borohydride, in order to obtain intermediates of the type (VII) which, through condensation with chloroacetylchloride, yield compounds of the general formula (II) wherein $A-Y = CH_2-R^2$.

$d_3$—Addition of HCN, liquid or dissolved in an inert solvent, in order to obtain the intermediates of type (VIII) which, by condensation with chloroacetylchloride, yield compounds of the general formula (II) wherein:

$$A-Y = \overset{R^2}{\underset{|}{CH}}-CN$$

Starting from the ortho-alkenyl substituted anilines indicated in Table 1, and by following one of the processes schematically summarized in Schemes 1 and 2, there were prepared the chloroacetanilides reported below in Table 2.

TABLE No. 2

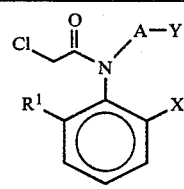

| Compound | R' | X | A—Y | B.p.(°C.) (mmHg) | C Calc. | C Found | H Calc. | H Found | N Calc. | N Found |
|---|---|---|---|---|---|---|---|---|---|---|
| 1 | $CH_3$ | $CH_2-CH=CH_2$ | $CH_2-O-CH_3$ | 115°(0.5) | 62.8 | 64.16 | 6.78 | 7.35 | 5.23 | 5.34 |
| 2 | $CH_3$ | $CH_2-CH=CH_2$ | $CH_2O-(CH_2)_3-CH_3$ | 151°-153°(0.1) | 65.9 | 64.96 | 7.81 | 7.69 | 4.52 | 4.65 |
| 3 | $C_2H_5$ | $CH_2-CH=CH_2$ | $CH_2O-CH_3$ | 142°(0.1) | 63.94 | 63.89 | 7.15 | 7.24 | 4.97 | 5.04 |
| 4 | $C_2H_5$ | $CH_2-CH=CH_2$ | $CH_2O-(CH_2)_3-CH_3$ | 160°(0.1) | 66.67 | 63.21 | 8.09 | 7.52 | 4.32 | 4.48 |
| 5 | $C_2H_5$ | $CH_2-CH=CH_2$ | $CH_2O-CH(CH_3)_2$ | 135°-139°(0.03) | 65.9 | 63.18 | 7.81 | 7.23 | 4.52 | 5.05 |

TABLE No. 2-continued

Structure: ClCH₂C(=O)N(A-Y)(aryl), where aryl is 2-R¹, 6-X-phenyl

| Compound | R' | X | A—Y | B.p.(°C.) (mmHg) | C Calc. | C Found | H Calc. | H Found | N Calc. | N Found |
|---|---|---|---|---|---|---|---|---|---|---|
| 6 | C₂H₅ | CH₂—CH=CH₂ | CH₂—C(=O)—OC₄H₉n | 180°–200°(0.4) | 64.85 | 64.16 | 7.45 | 7.59 | 3.98 | 4.13 |
| 7 | C₂H₅ | CH₂—CH=CH₂ | CH₂—C(=O)—O—CH(CH₃)₂ | — | 63.99 | 63.06 | 7.16 | 7.31 | 4.15 | 4.19 |
| 8 | C₂H₅ | CH₂—CH=CH₂ | CH₂—C(=O)—OC₂H₅ | — | 63.05 | 64.0 | 6.85 | 6.6 | 4.32 | 4.43 |
| 9 | CH₃ | CH₂—CH=CH₂ | CH₂OC(=O)—CH₃ | 162°–165°(0.1) | 60.91 | 60.58 | 6.13 | 6.22 | 4.73 | 5.1 |
| 10 | C₂H₅ | CH₃–CH—CH=CH₂ | CH₂—O—CH₃ | 150°–155°(0.3) | 64.97 | 63.93 | 7.5 | 7.2 | 4.73 | 4.9 |
| 11 | C₂H₅ | CH₃–CH—CH=CH₂ | CH₂—O—C₃H₇n | 155°–157°(0.1) | | | | | | |
| 12 | C₂H₅ | CH₃–CH—CH=CH₂ | CH₂—O—C₄H₉n | 165°–168°(0.2) | 67.54 | 65.37 | 8.35 | 7.98 | 4.14 | 4.62 |
| 13 | C₂H₅ | CH₃–CH—CH=CH₂ | CH₂—O—CH₂—(2-furyl) | 185°–187°(0.04) | 66.38 | 66.14 | 6.68 | 6.76 | 3.87 | 4.02 |
| 14 | C₂H₅ | CH₃–CH—CH=CH₂ | CH₂—CN | — | 66.3 | 64.08 | 6.6 | 6.84 | 9.65 | 8.79 |
| 15 | CH₃ | CH₂—CH=CH₂ | CH₂—CH₂—O—CH₃ | — | | 64.04 | 7.12 | 7.08 | 5.0 | 5.2 |
| 16 | CH₃ | CH₂—CH=CH₂ | CH₂—C(=O)—O—CH(CH₃)₂ | — | 63.05 | 66.47 | 6.85 | 6.98 | 4.32 | 4.42 |
| 17 | CH₃ | CH₂—CH=CH₂ | CH₂—C(=O)—O—CH₂—CH₃ | — | 62.03 | 62.07 | 6.51 | 6.68 | 4.52 | 4.56 |
| 18 | CH₃ | CH₂—CH=CH₂ | CH₂—C(=O)—O—C₄H₉n | — | 63.99 | 69.49 | 7.16 | 7.43 | 4.15 | 3.97 |
| 19 | CH₃ | CH₂—CH=CH₂ | CH₂—C(=O)—O—CH₃ | — | 60.91 | 58.64 | 6.13 | 5.88 | 4.74 | 4.26 |
| 20 | CH₃ | CH₂—CH=CH₂ | CH₂—O—C₃H₇ iso | — | 64.96 | 65.29 | 7.5 | 7.52 | 4.73 | 5.06 |
| 21 | CH₃ | CH₂—CH=CH₂ | CH₂—O—C₃H₇ | — | 64.96 | 66.39 | 7.5 | 7.53 | 4.73 | 4.77 |
| 22 | CH₂—CH=CH₂ | CH₂—CH=CH₂ | CH₂—O—CH₃ | — | 65.41 | 65.56 | 6.86 | 6.89 | 4.77 | 5.06 |
| 23 | CH₂—CH=CH₂ | CH₂—CH=CH₂ | CH₂—O—C₄H₉ n | — | 67.94 | 67.66 | 7.80 | 7.63 | 4.17 | 4.38 |
| 24 | CH₃ | CH₂—CH=CH₂ | CH₃–CH—CH₂—O—CH₃ | — | 64.96 | 65.06 | 7.5 | 7.4 | 4.73 | 4.85 |
| 25 | C₂H₅ | CH₂—CH=CH₂ | CH₂—CH₂—O—CH₃ | — | 64.96 | 63.18 | 7.5 | 7.29 | 4.73 | 4.8 |
| 26 | C₂H₅ | CH₂—CH=CH₂ | CH₃–CH—CH₂—O—CH₃ | — | 65.9 | 66.1 | 7.81 | 8.05 | 4.52 | 4.7 |
| 27 | CH₃ | CH=CH—CH₃ | CH₂OCH₃ | — | 62.8 | 63.48 | 6.78 | 6.92 | 5.23 | 5.48 |
| 28 | CH₃ | CH=CH—CH₃ | CH₂—O—CH(CH₃)₂ | 154°(0.1) | 64.96 | 67.47 | 7.5 | 7.85 | 4.73 | 4.96 |
| 29 | CH₃ | CH=CH—CH₃ | CH₂O-nC₄H₉ | 158°–160°(0.1) | 65.9 | 63.94 | 7.81 | 7.48 | 4.52 | 4.60 |
| 30 | C₂H₅ | CH=CH—CH₃ | CH₂OCH₃ | 144°–146°(0.05) | 63.94 | 64.03 | 7.15 | 7.25 | 4.97 | 5.35 |
| 31 | C₂H₅ | CH=CH—CH₃ | CH₂O—(CH₃)₂ | 159°–161°(0.7) | 65.90 | 66.75 | 7.81 | 7.83 | 4.52 | 5.1 |
| 32 | C₂H₅ | CH=CH—CH₃ | CH₂O-nC₄H₉ | 160°–163°(0.5) | 66.8 | 64.17 | 8.11 | 7.7 | 4.32 | 4.73 |
| 33 | CH=CH—CH₃ | CH=CH—CH₃ | CH₂OCH₃ | — | 65.41 | 65.08 | 6.86 | 6.7 | 4.77 | 5.15 |
| 34 | CH₃ | CH=CH—CH₃ | CH₂—CH₂OCH₃ | — | 63.93 | 66.29 | 7.15 | 7.82 | 4.97 | 5.43 |
| 35 | C₂H₅ | CH=CH—CH₃ | CH₂—CH₂OCH₃ | — | — | — | — | — | — | — |
| 36 | C₂H₅ | CH=CH—CH₃ | CH₃–CH—CH₂OCH₃ | — | 65.9 | 66.5 | 7.81 | 7.88 | 4.52 | 4.93 |
| 37 | CH₃ | CH=CH—CH₃ | CH₂—COOC₂H₅ | — | 62.03 | 63.35 | 6.51 | 6.71 | 4.52 | 4.62 |

The chloroacetanilides of the general formula (II) proved to have an excellent herbidical activity towards infesting monocotyledons and dicotyledons in pre-emergence phase (that is, when the infestant has not yet emerged from the soil).

The herbicidal activity of such compounds, examined by the method described below in Example 15, is recorded in Table 3, together with the activity of known chloroacetanilides derived from 2,6-dialkyl-anilines, such as for instance Alachlor and Antor.

The herbicidal activity is expressed on a value scale whose values range from 0 (=growth of the infestant in the presence of the herbicide equal to that of the witness infestant in the absence of herbicide) to 9 (total inhibition of the growth of the infestant). The data are reported in Table 3.

TABLE No. 3

Herbicide activity in pre-emergence, expressed on the basis of a scale of values ranging from 0 (no activity) to 9 (total activity).

| Compound | Dose KG/HA | Monocotyledones | | | | | | | | | | Dicotyledones | | | | | | | | | |
|---|---|---|---|---|---|---|---|---|---|---|---|---|---|---|---|---|---|---|---|---|---|
| | | Echino-chloa c.g. | Avena | Lol-ium | Sor-ghum | Set-aria | Digi-taria | Alope-curus | Pan-icum D. | Fes-tuca | Total | Stel-laria | Ipo-mea | Vig-na | Ru-mex | Galin-soga | Cap-sella | Sola-num | Gal-ium | Convol-volus A. | Total |
| 1 | 2 | 9 | 9 | 9 | 9 | 9 | 9 | 9 | 9 | 9 | 81 | 8 | 8 | 9 | 9 | 7 | 9 | 7 | 7 | 1 | 65 |
| | 1 | 9 | 8 | 8 | 9 | 9 | 9 | 9 | 9 | 9 | 79 | 8 | 5 | 7 | 9 | 7 | 9 | 4 | 3 | 1 | 53 |
| | 0.5 | 9 | 6 | 6 | 9 | 7 | 9 | 8 | 9 | 8 | 74 | 8 | 4 | 6 | 6 | 7 | 8 | 4 | 1 | 0 | 41 |
| | 0.25 | 9 | 5 | 8 | 8 | 5 | 9 | 6 | 9 | 8 | 65 | 6 | 4 | 6 | 5 | 6 | 7 | 4 | 0 | 0 | 38 |
| 2 | 2 | 9 | 7 | 8 | 9 | 9 | 9 | 8 | 9 | 9 | 77 | 8 | 3 | 8 | 8 | 9 | 9 | 8 | 2 | 3 | 58 |
| | 1 | 9 | 7 | 8 | 9 | 8 | 9 | 8 | 9 | 9 | 76 | 8 | 2 | 7 | 6 | 9 | 8 | 7 | 1 | 1 | 43 |
| | 0.5 | 9 | 4 | 6 | 8 | 5 | 8 | 5 | 9 | 8 | 63 | 3 | 1 | 4 | 5 | 6 | 5 | 3 | 0 | 0 | 25 |
| | 0.25 | 9 | 3 | 3 | 8 | 3 | 9 | 3 | 8 | 6 | 51 | 1 | | | | | | | | | |
| 3 | 2 | 9 | 9 | 9 | 9 | 9 | 9 | 9 | 9 | 9 | 81 | 8 | 5 | 9 | 9 | 9 | 8 | 9 | 5 | 3 | 65 |
| | 1 | 9 | 8 | 8 | 9 | 9 | 9 | 8 | 9 | 9 | 78 | 8 | 4 | 8 | 9 | 7 | 8 | 5 | 4 | 1 | 54 |
| | 0.5 | 9 | 6 | 7 | 8 | 7 | 9 | 8 | 9 | 8 | 71 | 6 | 4 | 6 | 6 | 6 | 7 | 3 | 2 | 0 | 40 |
| | 0.25 | 9 | 3 | 4 | 7 | 4 | 8 | 6 | 8 | 7 | 57 | 4 | 3 | 4 | 4 | 5 | 6 | 2 | 0 | 0 | 28 |
| 4 | 2 | 9 | 6 | 7 | 8 | 8 | 9 | 8 | 9 | 8 | 71 | 3 | 3 | 8 | 4 | 8 | 4 | 8 | 0 | 0 | 38 |
| | 1 | 9 | 5 | 5 | 7 | 6 | 8 | 7 | 8 | 5 | 60 | 2 | 2 | 5 | 3 | 6 | 4 | 6 | 0 | 0 | 28 |
| | 0.5 | 8 | 3 | 3 | 6 | 4 | 5 | 4 | 8 | 3 | 44 | | | | | | | | | | |
| | 0.25 | 7 | 3 | 3 | 5 | 3 | 4 | 2 | 8 | 2 | 37 | | | | | | | | | | |
| 5 | 2 | 9 | 8 | 9 | 9 | 9 | 9 | 9 | 9 | 9 | 80 | 7 | 6 | 7 | 5 | 9 | 9 | 7 | 8 | 2 | 60 |
| | 1 | 9 | 7 | 8 | 8 | 7 | 9 | 7 | 9 | 9 | 75 | 6 | 4 | 5 | 4 | 7 | 7 | 5 | 4 | 0 | 42 |
| | 0.5 | 9 | 5 | 7 | 7 | 6 | 7 | 5 | 8 | 8 | 65 | 4 | 2 | 3 | 3 | 4 | 5 | 4 | 1 | 0 | 26 |
| | 0.25 | 8 | 4 | 4 | 4 | 4 | 7 | 5 | 8 | 6 | 50 | | | | | | | | | | |
| Alachlor reference compound | 2 | 9 | 9 | 9 | 9 | 9 | 9 | 9 | 9 | 9 | 81 | 8 | 4 | 9 | 9 | 8 | 9 | 7 | 2 | 1 | 57 |
| | 1 | 9 | 8 | 9 | 9 | 9 | 9 | 8 | 9 | 9 | 79 | 8 | 4 | 7 | 9 | 8 | 8 | 3 | 0 | 0 | 47 |
| | 0.5 | 9 | 4 | 7 | 9 | 7 | 9 | 7 | 9 | 9 | 70 | 5 | 2 | 6 | 6 | 7 | 7 | 3 | 0 | 0 | 36 |
| | 0.25 | 9 | 3 | 6 | 8 | 5 | 8 | 6 | 9 | 8 | 62 | 4 | 1 | 4 | 4 | 5 | 6 | 1 | 0 | 0 | 25 |
| 10 | 2 | 9 | 7 | 9 | 9 | 9 | 9 | 9 | 9 | 9 | 79 | 7 | 3 | 8 | 9 | 7 | 9 | 7 | | | |
| | 1 | 9 | 5 | 8 | 7 | 8 | 9 | 7 | 9 | 7 | 74 | | | | | | | | | | |
| | 0.5 | 9 | 2 | 6 | 7 | 8 | 9 | 5 | 9 | 7 | 62 | | | | | | | | | | |
| | 0.25 | 9 | 0 | 5 | 6 | 6 | 5 | 3 | 7 | 6 | 47 | | | | | | | | | | |
| 8 | 2 | 9 | 6 | 9 | 9 | 8 | 9 | 9 | 9 | 9 | 77 | 3 | | | | | | | | Bromus Sp. | |
| | 1 | 9 | 5 | 8 | 8 | 6 | 9 | 6 | 8 | 7 | 64 | | | | | | | | | | |
| | 0.5 | 9 | 4 | 5 | 5 | 4 | 7 | 3 | 4 | 4 | 42 | | | | | | | | | | |
| 14 | 2 | 9 | 5 | 9 | 8 | 8 | 9 | 7 | 9 | 7 | 75 | 7 | | | | | | | | | |
| | 1 | 9 | 4 | 7 | 7 | 7 | 7 | 7 | 9 | 7 | 64 | | | | | | | | | | |
| 15 | 2 | 9 | 9 | 9 | 9 | 9 | 9 | 9 | 9 | 9 | 81 | 9 | | | | | | | | | |
| | 1 | 9 | 7 | 9 | 9 | 9 | 9 | 8 | 9 | 8 | 77 | 9 | | | | | | | | | |
| 17 | 2 | 9 | 7 | 9 | 8 | 7 | 9 | 7 | 9 | 7 | 76 | 9 | | | | | | | | | |
| | 1 | 9 | 5 | 9 | 8 | 3 | 5 | 8 | 9 | 7 | 64 | 9 | | | | | | | | | |
| 20 | 2 | 9 | 4 | 9 | 8 | 8 | 9 | 8 | 9 | 9 | 73 | 7 | | | | | | | | | |
| | 1 | 9 | 2 | 7 | 7 | 7 | 9 | 7 | 9 | 7 | 66 | 7 | | | | | | | | | |
| 22 | 2 | 9 | 7 | 9 | 9 | 7 | 9 | 9 | 9 | 7 | 73 | 9 | | | | | | | | | |
| | 1 | 7 | 4 | 7 | 7 | 7 | 9 | 7 | 9 | 7 | 66 | 7 | | | | | | | | | |
| 24 | 2 | 9 | 7 | 7 | 9 | 9 | 9 | 7 | 9 | 7 | 77 | 7 | | | | | | | | | |
| | 1 | 9 | 7 | 7 | 9 | 9 | 9 | 7 | 9 | 7 | 74 | 7 | | | | | | | | | |
| 27 | 2 | 9 | 4 | 7 | 9 | 9 | 9 | 7 | 9 | 7 | 73 | 7 | | | | | | | | | |
| | 1 | 9 | 4 | 7 | 7 | 9 | 9 | 4 | 9 | 7 | 65 | 7 | | | | | | | | | |

TABLE No. 3-continued
| | | Herbicide activity in pre-emergence, expressed on the basis of a scale of values ranging from 0 (no activity) to 9 (total activity). | | | | | | | | | | |
|---|---|---|---|---|---|---|---|---|---|---|---|---|
| 28 | 2 | 9 | 7 | 9 | 9 | 9 | 8 | 9 | 9 | 9 | 78 | 9 |
| 34 | 1 | 8 | 2 | 8 | 9 | 5 | 5 | 7 | 9 | 8 | 61 | 8 |
| 38(a) | 2 | 9 | 7 | 9 | 9 | 9 | 8 | 9 | 9 | 9 | 78 | 9 |
| 39(b) | 1 | 9 | 5 | 9 | 7 | 7 | 8 | 9 | 7 | 9 | 74 | 9 |
| 39 | 2 | 9 | 7 | 9 | 9 | 9 | 9 | 9 | 9 | 9 | 79 | 9 |
| 40(c) | 1 | 9 | 6 | 9 | 8 | 8 | 7 | 9 | 9 | 9 | 78 | 9 |
| | 2 | 9 | 4 | 9 | 7 | 7 | 9 | 9 | 4 | 9 | 76 | 9 |
| Antor (reference compound offenlegungsch 2.311.897) | 2 | 9 | 8 | 7 | 9 | 9 | 9 | 9 | 8 | 9 | 67 | 9 |
| | 1 | 9 | 7 | 7 | 9 | 7 | 7 | 9 | 7 | 9 | 79 | 9 |
| | 0.5 | 9 | 5 | 5 | 7 | 5 | 5 | 9 | 6 | 7 | 73 | 9 |
| | 0.25 | 9 | 3 | 4 | 3 | 3 | 3 | 6 | 4 | 5 | 60 | 9 |
| | | | | | | | | | | | 40 | |
(a)38 = 2-methyl-6-allyl-N-ethoxymethyl-chloroacetanylide
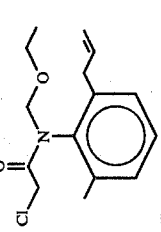
(b)39 = 2-methyl-6-allyl-N-ethoxyethyl-chloroacetanylide
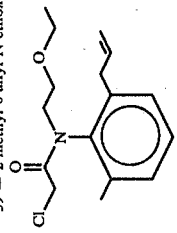
(c)40 = 2,6-diallyl-N-ethoxymethyl-chloroacetanylide
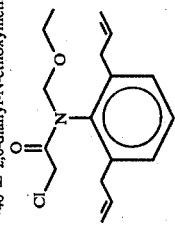

In comparison with the known chloroacetanilides derived from 2,6-dialkyl anilines, the chloroacetanilides of this invention offer the great advantage of being more selective, since they do not do any harm to important agricultural crops such as for instance maize.

The toxicity for some useful agricultural crops has been checked by means of the method described in Example 16. The data are recorded below in Table 4 together with the toxicity for maize and wheat developed by the chloroacetanilides known as Alachlor and Antor. The toxicity is expressed in terms of a scale of values ranging from 0 (no damage; growth equal to that of the witness plant) to 9 (full damage with total inhibition of growth).

Toxicity on useful crops expressed in terms of a scale of values ranging from 0 (no damage) to 9 (full damage).

| Compound | dose (kg/ha) | Maize | Wheat | Beetroots |
|---|---|---|---|---|
| 2 | 4 | 2 | — | |
|   | 2 | 0 | 4 | |
| 4 | 4 | 0 | — | |
|   | 2 | 0 | 2 | |
| 5 | 4 | 0 | — | |
|   | 2 | 0 | 7 | |
| 7 | 4 | 0 | — | |
|   | 2 | 0 | 6 | |
| 11 | 4 | 1 | — | |
|   | 2 | 0 | 4 | |
| 22 | 4 | 0 | | 0 |
| 24 | 4 | 0 | | 0 |
| 27[a] | 4 | 0 | | |
| 34 | 4 | 0 | | 0 |
| 39[b] | 4 | 0 | | 0 |
| Alachlor (witness product). | 4 | 7 | — | |
|   | 2 | 5 | 7 | |
| Antor (witness product. DOS 2,311,897) | 4 | 7 | 9 | |
|   | 2 | 5 | 9 | |

[a]Toxicity on cotton = 3 (4 kg/ha):
[b]39 = 2-methyl-6-allyl-N-ethoxymethyl-chloroacetanilide

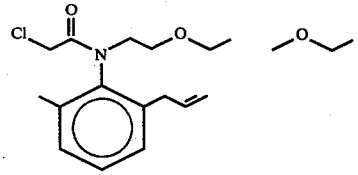

In order still better to illustrate this invention, the following examples are given, without limiting purposes:

EXAMPLE 1

Preparation of 2-ethyl-6-allyl-aniline (compound A, Table 1)

64 g (0.4 moles) of 2-ethyl-N-allylaniline, 56 g of finely ground anhydrous $ZnCl_2$ and 120 ml of anhydrous xylene were introduced into a flask connected to a reflux condenser and a calcium chloride dehydrator. The contents were then heated at reflux temperature for 4 hours.

After cooling down to 60° C., to the mixture were added 70 g of NaOH in 400 ml of water. This reaction mixture was then extracted at room temperature with diethyl ether and the etheric extract was then dehydrated by means of $Na_2SO_4$.

After removal of the ether by evaporation, the extract was subjected to distillation to recover the xylene and to collect the fraction boiling at between 125° and 140° C. at 15 mm Hg.

This fraction, amounting to 51 g, consisted mainly of 2-ethyl-6-allyl-aniline (as determined by gas-chromatographic analysis).

A small aliquot of the distilled fraction was chromatographed on silica gel (eluent: 95% benzene, 5% diethylether).

Then the intermediate fraction was collected, equal to 70% of the eluted quantity and the analytical determinations were carried out on this (Elemental analysis, I.R., and NMR).

EXAMPLES 2-4

Following the procedure as described in Example 1, and starting from the appropriate 2-alkyl-N-2'-alkenyl-aniline, the 2-alkyl-6-(2'-alkenyl) anilines indicated below were prepared:

EXAMPLE 2: 2-methyl-6-allyl-aniline

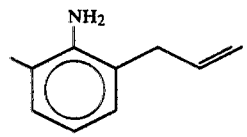

(compound B, Table 1)

EXAMPLE 3: 2-ethyl-6-(1'-methyl-2'-propenyl)-aniline

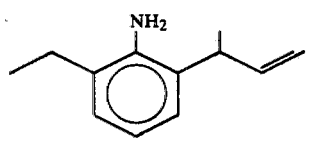

(compound C, Table 1)

EXAMPLE 4:
2-methyl-6-(1'-methyl-2'-propenyl)-aniline

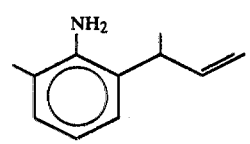

(compound D, Table 1)

EXAMPLE 5

3 g (0,02 moles) of N-allyl-2-methyl-aniline and 20 ml of a 2 N solution of $H_2SO_4$ were introduced into a Carius tube of 100 ml capacity. The tube was then flame-sealed and maintained at 150° C. for 2 hours.

After cooling down, the contents were poured into a diluted NaOH solution in a quantity sufficient to give an alkaline pH, and then extracted with diethylether.

The extract, after drying over $Na_2SO_4$ and evaporation of the solvent, was distilled at reduced pressure.

Thereby were obtained 2.5 g of 2-methyl-6-allyl-aniline (compound B, Table 1).

EXAMPLES 6-7

The reaction described in Example 5 was repeated, salifying the N-allyl-2-methyl-aniline with a stoichiometric quantity of a 1 M aqueous solution of HCl, and by applying the same temperature and time conditions for the heating.

After treatment of the contents according to the procedure described in Example 5, there was obtained a distillate consisting of 2 g of 2-methyl-6-allyl-aniline.

The same reaction was repeated by salifying N-allyl-2-methyl-aniline with an equimolecular quantity of a 3 N-solution of $H_3PO_4$ and by applying the same conditions of temperature for a period of 6 hours.

At the end, after extraction of the aqueous alkali-treated product with diethylether, there was obtained a mixture containing 50% of the starting aniline and 50% of 2-methyl-6-allyl-aniline.

EXAMPLE 8

20 g (0.098 moles) of N-allyl-N-methoxyethyl-ortho-toluidine and 100 ml of an aqueous 2 N-solution of $H_2SO_4$ were introduced into a Carius tube of 100 ml capacity. The tube was flame-sealed after which it was heated at a temperature of 130° C. for 3 hours. After cooling down, the contents of the tube were treated as described above in Example 5. There was thus obtained 13 g of N-methoxyethyl-2-methyl-6-allyl-aniline whose characteristics are recorded in Table 1 (compound F).

EXAMPLE 9

By operating as described in Examples 5 and 8 but starting from N-diallyl-aniline, 2,6-diallyl-aniline was obtained with 70–80% yield. Its characteristics are recorded in Table 1 (compound E).

EXAMPLE 10

30 g of 2-methyl-6-allyl-aniline and 60 g of KOH dissolved in 120 g of ethylene glycol were introduced into a 250 ml flask equipped with a stirrer and a reflux condenser. The reaction mixture was stirred for 3 hours at 160° C. After cooling down, the reaction mixture was additioned with 100 ml of benzene and was then left under stirring for 15 minutes.

The benzenic phase was separated and washed with water and then dehydrated over $Na_2SO_4$.

The solvent was removed and the residue distilled under vacuum, collecting 22 g of a fraction boiling between 126° and 130° C. at a pressure of 20 mm Hg. This fraction consisted of 2-methyl-6-(1'-propenyl)-aniline whose characteristics are reported in Table 1 (compound J).

EXAMPLE 11

Preparation of 2-methyl-6-allyl-N-methoxy-methyl-chloroacetanilide (compound 3, Table 2).

Into a 250 ml flask, fitted with a Marcusson, were introduced:

25 g of the distillate with a boiling point between 125° and 140° C. (at 15 mm Hg), obtained as described in Example 1, and consisting mostly of 2-ethyl-6-allyl-aniline;

18 g of trioxane in 40 ml of benzene; and 2 ml of a methanolic solution of triethylamine at 25% concentration.

The reaction mixture was then heated and maintained at reflux temperature until the water, formed during the reaction, had been completely eliminated as an azeotrope. At this point, the temperature was brought to 100°–110° C. and maintained at this level for half an hour.

Thereupon the reaction mixture was distilled, collecting 13 g of a fraction boiling at 120°–122° C. at a pressure of 20 mm Hg, and which consisted of N-methylene-2-ethyl-6-(2'-propenyl)-aniline.

4 g of this intermediate were then additioned in a 100 ml flask to 2.6 g of chloroacetylchloride dissolved in 20 ml of benzene. The temperature increased up to 60° C. After allowing the reaction mixture to cool down to room temperature, there were then added 10 ml of methanol containing 2.3 g of triethylamine.

The reaction mixture was then allowed to stand for 14 hours, after which it was poured into water and the organic phase was extracted with diethyl-ether.

The extract was then dehydrated with $CaCl_2$ and, after evaporation of the solvent, the residue was distilled to give 5 g of 2-ethyl-6-allyl-N-methoxymethyl-chloroacetanilide (oil, boiling point = 142° C. at 0.1 mm Hg).

EXAMPLE 12

Preparation of N-(carbobutoxymethyl)-2-ethyl-6-allyl-chloroacetanilide (compound 6, Table 2).

7 g of the distillate containing 2-ethyl-6-allyl-aniline obtained as described in Example 1, 13 g of n-butyl-chloroacetate in 40 ml of dimethylformamide, 7.3 g of $NaHCO_3$ and 0.2 g of potassium iodide were introduced into a 100 ml flask equipped with a reflux condenser.

The reaction mixture was then heated at reflux temperature for 4 hours. After cooling down, the contents were poured into water and extracted with diethylether. This extract was then dehydrated over $Na_2SO_4$ and, after evaporation of the solvent, the residue was distilled under vacuum to collect the fraction boiling at between 130° and 150° C. at 0.1 mm Hg. This fraction (7.3 g) consisted of N-(carbobutoxymethyl)-2-ethyl-aniline as main component (by gas-chromatographic analysis).

7.2 g of this fraction were thereupon transferred to a 100 ml flask fitted with a stirrer and a reflux condenser, and additioned with 50 ml of benzene and 4.5 g of $NaHCO_3$. Then 3 g of chloroacetylchloride were slowly added dropwise at room temperature and under vigorous stirring.

The reaction mixture was thereupon heated for 3 hours at reflux temperature. After cooling down, the contents were washed first with 200 ml of water and then with 200 ml of HCl diluted in a ratio of 1:1.

The organic phase was then extracted with diethylether, dehydrated over $Na_2SO_4$ and, after evaporation of the ether, subjected to distillation under vacuum in order to recover the benzene and for collecting the fraction boiling between 180° and 200° C. at 0.1 mm Hg.

This fraction amounted to 3.5 g of N-(carbobutoxymethyl)-2-ethyl-6-allyl-chloroacetanilide whose characteristics are reported above in Table 2.

EXAMPLE 13

Preparation of N-cyanomethyl-2-ethyl-6-(1'-methyl-2'-propenyl)-chloroacetanilide (compound 14, Table 2).

Into a 250 ml flask, fitted with a Marcusson, were introduced:

35 g of a distillate containing 2-methyl-6-(1'-methyl-propenyl)-aniline, obtained according to the process described in Example 3;

23 g of trioxane in 50 ml of benzene; and 3 ml of a methanolic solution of triethylamine (25% concentration).

This reaction mixture was then heated at reflux temperature until the water formed during the reaction was completely eliminated.

At this point, the temperature was brought up to 130° C. and maintained at that value for half an hour. After cooling down, the mixture was then distilled under vacuum and the fraction boiling at 127° C. at 18 mm Hg was collected. This fraction amounted to 16 g and consisted of N-methylene-2-ethyl-6-(1'-methyl-2'-propenyl)-aniline.

1.4 g of KCN and 30 ml of benzene were introduced into a 100 ml flask equipped with a stirrer and a reflux condenser. While maintaining the temperature at 0° C., 1.3 g of glacial acetic acid were added dropwise. The contents of the flask were then brought to room temperature and, under vigorous stirring, there were rapidly added to it 4 grams of N-methylene-2-ethyl-6-(1'-methyl-2'-propenyl)-aniline.

The contents of the flask were then heated at reflux temperature for 4 hours. After cooling, the reaction mixture was poured into 200 ml of water and the organic phase was extracted with diethylether. The extract was dehydrated and, after evaporation of the ether, was distilled under vacuum in order to recover the benzene and to collect the fraction boiling at 128° C. at a pressure of 0.3 mm Hg.

This fraction amounted to 1 g and consisted of N-cyanomethyl-2-ethyl-6-(1'-methyl-2'-propenyl)-aniline. The I.R. analysis showed the following results:
$\nu(NH):3392$ cm$^{-1}$; $\nu(C\equiv N):2220$ cm$^{-1}$; $\nu(C=C):1630$ cm$^{-1}$; $\nu(CH=CH_2):990, 910$ cm$^{-1}$.

By condensation of the intermediate thus obtained with chloroacetylchloride in benzene and in the presence of NaHCO$_3$, 1 g of N-cyanomethyl-2-ethyl-6-(1'-methyl-2-propenyl)-chloroacetanilide was obtained.

EXAMPLE 14

Preparation of N-methoxymethyl-2-methyl-6-(1-propenyl)-chloroacetanilide (compound 27, Table 2).

Into a 100 ml flask fitted with a Marcusson, were placed:

6.8 g of 2-methyl-6-(1-propenyl)-aniline obtained as described in Example 10;

5 g of trioxane in 10 ml of benzene; and 0.5 g of a methanolic solution of triethylamine (25% concentration).

The reaction mixture was then reflux-heated until the complete azeotropic distillation away of the water formed during the reaction. At this point the temperature was raised to between 100° and 110° C. and maintained within that range for half an hour. Thereafter the solvent and the unreacted trioxane were removed under vacuum.

The residue, consisting of raw N-methylene-2-methyl-6-(1-propenyl)-aniline, was then diluted with benzene (15 ml) and the solution was additioned with a solution of chloroethylchloride in benzene (7.1 g in 10 ml).

During the additioning the temperature rose up to 45° C. After allowing the reaction mixture to cool down to room temperature, it was additioned with 20 ml of methanol containing 4.5 g of triethylamine. The reaction mixture was then allowed to stand for 14 hours, then it was poured into water and extracted with diethylether, the extract dehydrated over CaCl$_2$, and the solvent evaporated.

The raw oil thus obtained was purified by chromotography on silica gel (eluant:benzene/diethylether 9:1).

Thereby were obtained 3.5 g of N-methoxymethyl-2-methyl-6-(1-propenyl)-chloroacetanilide.

EXAMPLE 15

Herbicidal activity with pre-emergence intervention

Pots with an upper diameter equal to 10 cm and a height equal to 10 cm were filled with a sandy soil and in each of them was sown one of the following infestants:

*ECHINOCHLOA CRUS-GALLI, AVENA FAUA, LOLIUM SP, SORGHUM SP, PANICUM DICHOTOMIFLORUM, DIGITARI SANGUINALIS, ALOPECURUS MYOSUROIDES, FESTUCA SP., STELLARIA MEDIA, IPOMEA SP., VIGNA SINENSIS, RUMEX CRISPUS, GALINSOGA SP., CAPSELLA BURSA PASTORIS, CONVOLVOLUS ARVENSIS, GALIUM APARINE, SOLANUM NIGRUM, BROMUS SP..*

The amount of water necessary for good germination of the seeds was added to each pot. Said pots were then treated with each of the herbicides in the form of an aqueous acetone dispersion (20% vol./vol.) by application to the surface of the soil, and then were covered with a layer of 0.5 cm of soil.

All the pots were kept under observation in a conditioned environment, at a temperature between 15° C. and 24° C., a relative humidity of 70%, a photo-period of 12 hours, and a luminous intensity of 2500 lux. Every two days all the pots were uniformly sprinkled with water so as to ensure a sufficient degree of humidity for a good growth of the seedlings.

After 28 days from the date of treatment the vegetative state (stage of the growth) of the plants was checked, with evaluations expressed on the basis of a scale of values ranging from 0 (=growth equal to that of the witness plant) up to 9 (=complete stoppage of growth).

The data thus obtained are recorded above in Table 3.

EXAMPLE 16

The compounds of the invention were tested in order to ascertain their toxicity on useful agricultural crops, under the following conditions:

Pots with an upper diameter of 10 cm and a height of 10 cm were filled with sandy soil in which were then sown seeds of maize, wheat, beets and cotton, separately. To each pot was then added water in an amount sufficient for good germination of the seeds. Said pots were then treated with each of the herbicides in the form of an aqueous acetone dispersion (20% vol./vol.) applied to the surface of the soil, and then were covered up with a layer of soil of 0.5 cm.

All the pots were maintained under observation in a conditioned environment at a temperature between 15° and 24° C., a relative humidity of 70%, a photo-period of 12 hours, and a luminous intensity of 2500 lux. Every two days, all pots were uniformly watered so as to insure a degree of humidity sufficient for good growth of the plants.

After 28 days from the time of treatment the vegetative state of the plants was checked and the evaluations were expressed on the basis of a scale of values ranging from 0 (growth equal to that of the witness plant) up to 9 (complete stoppage of growth).

Data thus obtained are reported above in Table 4.

What is claimed is:

1. A chloroacetanilide of the general formula:

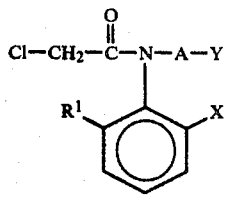

wherein:

$R^1$ = H, or alkyl with 1-5 carbon atoms, or X;
X = alkenyl, and preferably

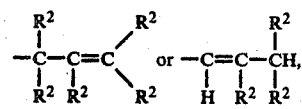

in which the various $R^2$, which may be equal to or different from each other, are H or an alkyl with 1-3 carbon atoms;

A = alkylene, optionally substituted, of the formula:

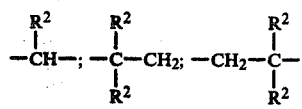

in which the various $R^2$, which may be equal to or different from each other, have the meanings specified above; and Y = H; alkyl with 1-5 carbon atoms; alkenyl with 2-5 carbon atoms; alkinyl with 2-5 carbon atoms; phenyl; cycloalkyl with 3-8 carbon atoms; halogen; CN; OR; SR;

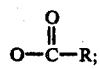

NHR; N(R)$_2$;

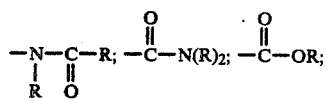

wherein R = H; alkyl with 1-5 carbon atoms; alkenyl or alkinyl with 2-5 carbon atoms; cycloalkyl with 3-8 carbon atoms; phenyl.

2. A compound as defined in claim 1, which is 2-methyl-6-allyl-N-methoxymethyl-chloroacetanilide.

3. A compound as defined in claim 1, which is 2-methyl-6-allyl-N-butoxymethyl-chloroacetanilide.

4. A compound as defined in claim 1, which is 2-ethyl-6-allyl-N-methoxymethyl-chloroacetanilide.

5. A compound as defined in claim 1, which is 2-ethyl-6-allyl-N-butoxymethyl-chloroacetanilide.

6. A compound as defined in claim 1, which is 2-ethyl-6-allyl-N-isopropoxymethyl-chloroacetanilide.

7. A compound as defined in claim 1, which is 2-ethyl-6-(1'-methyl-2'-propenyl)-N-methoxymethyl-chloroacetanilide.

8. A compound as defined in claim 1, which is N-(methoxymethyl)-2-methyl-6-(1-propenyl)-chloroacetanilide.

9. A compound as defined in claim 1, which is N-(isopropoxymethyl)-2-methyl-6-(1-propenyl)-chloroacetanilide.

10. A compound as defined in claim 1, which is N-(n.butoxymethyl)-2-ethyl-6-(1-propenyl)-chloroacetanilide.

11. A compound as defined in claim 1, which is N-(isopropoxymethyl)-2-ethyl-6-(1-propenyl)-chloroacetanilide.

12. A compound as defined in claim 1, which is N-(methoxymethyl)-2,6-bis-(1-propenyl)-chloroacetanilide.

13. A compound as defined in claim 1, which is N-(1-methyl-2-methoxyethyl)-2-ethyl-6-(1-propenyl)-chloroacetanilide.

14. A compound as defined in claim 1, which is N-(carboethoxymethyl)-2-methyl-6-(1-propenyl)-chloroacetanilide.

15. 2-Allyl-6-methyl-N-(methoxyethyl)-aniline.

16. 2-Allyl-6-ethyl-N-(methoxyethyl)-aniline.

17. 2-Allyl-6-methyl-N-(1-methyl-2-methoxyethyl)-aniline.

18. 2-Allyl-6-ethyl-N-(1-methyl-2-methoxyethyl)-aniline.

19. N(methoxyethyl)-2-(1-propenyl)-6-methyl-aniline.

20. A method for fighting infestations of infesting monocotyledons and dicotyledons during pre-emergence, this method consisting in spreading on the soil adjacent thereto a compound according to claim 1, in a quantity ranging from 0.25 kg/ha upwards.

* * * * *